United States Patent
Chang et al.

[11] 3,931,303
[45] Jan. 6, 1976

[54] PROCESS FOR PREPARING 5-HALO-2,3-PHENYLENEDIAMINE-1-CARBOXYLIC ACID

[75] Inventors: Charles H. Chang, Loudonville, N.Y.; David I. Randall, Easton, Pa.

[73] Assignee: GAF Corporation, New York, N.Y.

[22] Filed: June 28, 1973

[21] Appl. No.: 374,574

[52] U.S. Cl. ............................... 260/518 A; 71/114
[51] Int. Cl.² ........................................ C07C 101/68
[58] Field of Search .............................. 260/518 A

[56] References Cited
UNITED STATES PATENTS
3,158,646  11/1964  Dorfman et al................ 260/518 A

*Primary Examiner*—Lorraine A. Weinberger
*Assistant Examiner*—L. A. Thaxton
*Attorney, Agent, or Firm*—Walter C. Kehm

[57] ABSTRACT

Method of preparing 5-halo-2,3-phenylenediamine-1-carboxylic acids having the following formula:

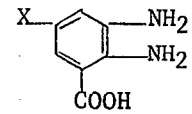

I wherein X is Cl, Br or F by reacting a 2,5-dihalo-3-nitrobenzoic acid with ammonium hydroxide to yield 5-halo-3-nitro anthranilic acid followed by a reduction of the resultant product. The 5-halo-2,3-phenylenediamine-1-carboxylic acids are useful as herbicides and as intermediates for use in the preparation of dyestuffs, photographic developers, pharmaceuticals, antioxidants and the like.

7 Claims, No Drawings

PROCESS FOR PREPARING 5-HALO-2,3-PHENYLENEDIAMINE-1-CARBOXYLIC ACID

This invention relates to a method of preparing 5-halo-2,3-phenylenediamine-1-carboxylic acid. It has already been proposed (Helv. Chim. Acta 40, 369) that 2,3-phenylenediamine carboxylic acid be prepared by hydrogenation of 2 amino-4-chloro-3-nitrobenzoic acid according to the following reaction scheme:

Nitration of chloro nitro benzoic acid

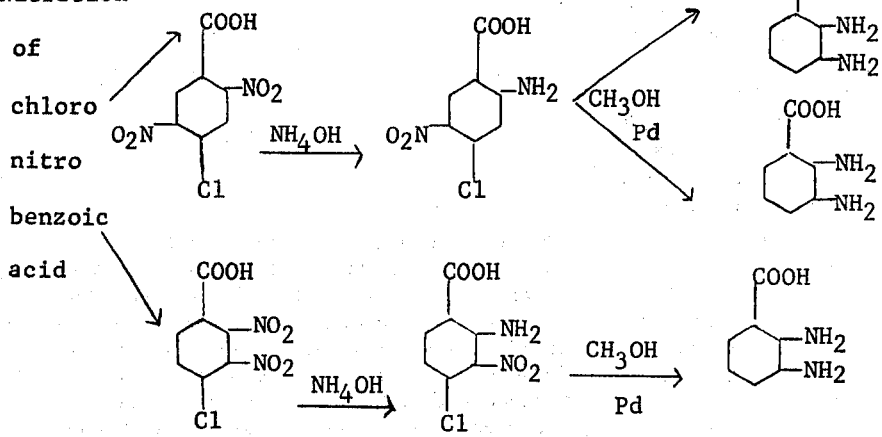

In accordance with the invention the process for preparing 5-halo-2,3-phenylenediamine-1-carboxylic acid having the following formula:

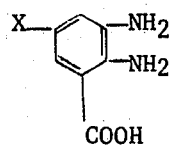

I wherein X is either chlorine, bromine or fluorine, are prepared by the reaction of a 2,5-dihalo-3-nitrobenzoic acid such as, for example, 2,5,dichloro,2,5dibromo- or 2,5-difluoro-3-nitrobenzoic acid with concentrated ammonium hydroxide in an autoclave at a temperature of about 125°–140°C to yield 5-halo-3-nitro anthranilic acid followed by reduction of the resultant product to yield 5-halo-3-amino anthranilic acid. The reaction in accordance with the invention takes place according to the following reaction scheme:

As is clear from the above, the process of the invention differs from the process set out above as the state of the art, in that in accordance with the invention, the ammonia preferentially replaces the Cl while in the reference, it replaces $NO_2$. Further, in accordance with the invention, the reduction reduces the nitro group leaving the chlorine atom intact while in the reference the reduction also eliminates the chlorine atom.

The compounds of the invention can be used directly as herbicides or can be used as intermediates for the preparation of dyestuffs, photographic developers, pharmaceuticals and the like. Thus, for example, the 5-halo-3-amino anthranilic acid can be reacted with either oxalic acid in the presence of hydrochloric acid or reacted with ethyl oxalate to convert the starting material into the 2,3-dihydroxy-7-haloquinoxaline-5-carboxylic acid. The latter is then reacted with a mixture of phosphorus pentachloride and phosphorus oxytrichloride or a mixture of phosphorus pentabromide and phosphorus oxytribromide under reflux to yield the haloquinoxaline carboxylic acid derivatives useful as herbicidal materials.

Alternatively, the compounds of the invention can be used as an intermediate in the production of reactive dyes as follows:

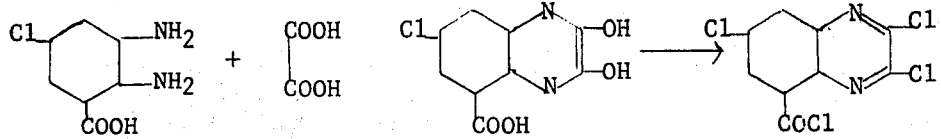

This is then reacted with an amine-containing dyestuff to produce a reactive dye.

The following examples are given for further illustrating the invention, but are nowise to be construed as limiting the scope thereof.

EXAMPLE 1

A mixture of 150 g. of 2,5-dichloro-3-nitrobenzoic

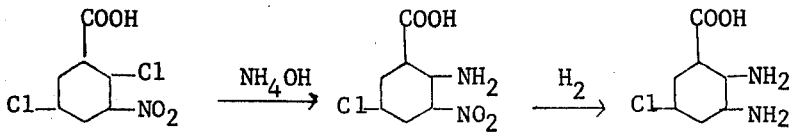

acid and 350 ml. of concentrated NH₄OH was heated in an autoclave at 130°C for 3 hours. The resulting mixture was acidified with 250 ml. concentrated HCl, filtered, washed with water and dried. There were thereby obtained 132 g. of 2-amino-5-chloro-3-nitrobenzoic acid also known as 5-chloro-3-nitroanthranilic acid having a melting point of 248°–250°C.

EXAMPLE 2

32.5 g. (0.15 mole) 2-amino-5-chloro-3-nitrobenzoic acid, prepared as set out in Example 1, were dissolved in sodium hydroxide solution, stirred with 1 g. Raney nickel for 10 minutes and filtered. The filtrate which was then recovered was acidified with glacial acetic acid to provide a pH of 6–7. 2 g. PtO (Adam's catalyst) were introduced into the filtrate and hydrogen gas passed in under a pressure of 45 psi gauge at 45°C for 6 hours. The bright yellow color of the filtrate disappeared during the subsequent reaction. The reaction mixture was then filtered to separate off the catalyst, acidified with glacial acetic acid to a pH of 6–7 and again filtered. This filtrate was extracted three times using 200 ml. portions of ether for each extraction and the ether extracts combined and evaporated. 24 g. of a dark, solid material (5-chloro-2,3-phenylenediamine carboxylic acid) were thereby obtained having a melting point of 207°–208°C.

EXAMPLE 3

A mixture of 47.2 g. (0.2 mole) 2,5-dichloro-3-nitrobenzoic acid, 50 ml. ammonium hydroxide and 100 ml. water was heated in a closed system using a water bath at 90°C for 12 hours. The yellow liquid reaction product was acidified with 50 ml. concentrated hydrochloric acid, filtered and washed with water. The paste consisting of the mono nitro intermediate which was thereby obtained was used directly for reduction to the corresponding amino compound.

The mono nitro intermediate was added in two portions to 69 g. (0.3 mole) of SnCl₂. 2H₂O in 100 ml. concentrated hydrochloric acid at 90°–100°C. The resulting reaction mixture was stirred for one half hour at 95°C, cooled to 10°C and then filtered. The recovered material was washed with 15 ml. benzene yielding 68 g. of wet cake containing the reaction product in the form of dihydrochloride. The 5-chloro-2,3-phenylenediamine carboxylic acid dihydrochloride was dried, dissolved in water, the solution made akaline with ammonium hydroxide, extracted with ether and the ether evaporated to produce a dark product having a melting point of 207°–208°C.

EXAMPLE 4

58.6 g. (0.2 mole) 2,5-dibromo-3-nitrobenzoic acid, 50 ml. ammonium hydroxide and 100 ml. water were heated together in a closed system over a water bath at 90°C for 12 hours. The reaction product thereby obtained was further worked up and hydrogenated according to the method of Example 3 to yield 5-bromo-2,3-phenylenediamine carboxylic acid in the form of a dark colored product.

We claim:

1. A process for preparing 5-halo-2,3-diamino benzoic acids having the formula:

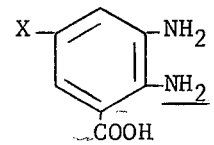

wherein X is a member selected from the group consisting of chlorine, bromine and fluorine which comprises the high temperature reaction of 2,5-dihalo-3-nitrobenzoic acid with ammonium hydroxide at a temperature of 125° and 140°C. to produce 5-halo-3-nitroanthranilic acid and reducing said 5-halo-3-nitroanthranilic acid to 5-halo-2,3-diamino benzoic acid.

2. Method according to claim 1 which comprises reacting said nitrobenzoic acid with ammonium hydroxide in an autoclave at a temperature of 125°–140°C.

3. Method according to claim 1 which comprises reducing said 5-halo-3-nitroanthranilic acid by treatment with stannous chloride and hydrochloric acid.

4. Method according to claim 1 which comprises reducing said 5-halo-3-nitrobenzoic acid by treatment with hydrogen in the presence of Raney nickel catalyst.

5. A 5-halo-2,3-phenylenediamine-1-carboxylic acid having the formula:

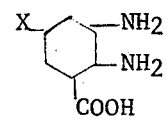

wherein X is a member selected from the group consisting of chlorine, bromine and fluorine.

6. Compound according to claim 5 designated 5-chloro-2,3-phenylenediamine benzoic acid.

7. Compound according to claim 5 designated 5-bromo-2,3-phenylenediamine benzoic acid.

* * * * *